United States Patent [19]
Kothe et al.

[11] Patent Number: 4,644,056
[45] Date of Patent: Feb. 17, 1987

[54] METHOD OF PREPARING A SOLUTION OF LACTIC OR COLOSTRIC IMMUNOGLOBULINS OR BOTH AND USE THEREOF

[75] Inventors: Norbert Kothe, Kronberg; Herbert Dichtelmüller, Sulzbach; Wolfgang Stephan, Dreieich; Bertram Eichentopf, Bad Soden, all of Fed. Rep. of Germany

[73] Assignee: Biotest Pharma GmbH, Frankfurt, Fed. Rep. of Germany

[21] Appl. No.: 772,070

[22] Filed: Sep. 3, 1985

[30] Foreign Application Priority Data

Sep. 6, 1984 [DE] Fed. Rep. of Germany ....... 3432718

[51] Int. Cl.$^4$ .......................... C07K 3/26; C07K 3/28; C07K 35/20
[52] U.S. Cl. ...................... 530/387; 424/85; 530/361; 530/414; 530/420; 530/832
[58] Field of Search ............... 260/112 R, 112 B, 120, 260/122; 424/85; 530/387, 361, 414, 420, 832

[56] References Cited

U.S. PATENT DOCUMENTS

| 4,018,752 | 4/1977 | Buhler et al. | 260/122 X |
|---|---|---|---|
| 4,051,235 | 9/1977 | Plymate | 424/85 |
| 4,265,924 | 5/1981 | Buhler et al. | 260/122 |
| 4,377,569 | 3/1983 | Plymate | 424/85 |
| 4,436,658 | 3/1984 | Peyrouset et al. | 260/112 R X |
| 4,490,290 | 12/1984 | Gani et al. | 260/112 R X |
| 4,526,715 | 7/1985 | Kothe et al. | 260/112 B |

FOREIGN PATENT DOCUMENTS

| 0085005 | 8/1983 | European Pat. Off. | |
| 2813984 | 10/1978 | Fed. Rep. of Germany. | |
| 3218348 | 12/1982 | Fed. Rep. of Germany. | |
| 0075433 | 4/1985 | Japan | 260/112 R |
| 1573995 | 9/1980 | United Kingdom. | |

Primary Examiner—Howard E. Schain
Attorney, Agent, or Firm—Sprung Horn Kramer & Woods

[57] ABSTRACT

A method of preparing a solution of lactic or colostric immunoglobulins or both by processing milk or colostrum or both accompanied by precipitation of the caseins, characterized in that milk or colostrum or both are acidified to a pH of 4.0–5.5, subjected to cross-flow filtration in a filtration unit with a mean pore size of 0.1–1.2 μm, and the low-molecular components removed by means of further cross-flow filtration in another filtration unit with a limit of separation of 5 000–80 000 daltons, as well as an agent for treating bacterial and viral infections that consists of a solution obtained by means of said method.

12 Claims, 2 Drawing Figures

METHOD OF PREPARING A SOLUTION OF LACTIC OR COLOSTRIC IMMUNOGLOBULINS OR BOTH AND USE THEREOF

The invention concerns both a method of preparing a solution of lactic or colostric immunoglobulins or both by processing milk (lactic milk) or colostrum (colostric milk) or both accompanied by precipitation of the caseins and an agent for treating bacterial and viral intestinal infections that consists of the resulting immunoglobulin solution.

Previous methods of harvesting immunoglobulins from milk or colostrum have been very inconvenient. The most common method for example consists of several steps. The fat is separated from the milk by centrifuging. The casein is acidified to precipitate it and separated out by more centrifuging. The pH is adjusted to its original value. The material is centrifuged once again to separate the precipitate resulting from pH adjustment. This results in a lactoserum, from which the immunoglobulins are precipitated by dilution with ammonium sulfate. The resulting precipitate is separated by centrifuging, dissolved in water, and filtration sterilized. The ammonium sulfate is removed by dialysis and the resulting solution filtration sterilized again and bottled. The whole process takes at least three days.

European Pat. No. 85 005 discloses a method of harvesting immunoglobulin from colostrum in which the colostrum or preferably colostric serum is subjected to electrophoresis and the immunoglobulin-rich fraction fractionated by chromatography on ion exchangers. The effluate from this fractionation is rich in a larger proportion of the immunoglobulins. This method, however, is also very inconvenient and time-consuming.

German Offenlegungsschrift No. 3 218 348 discloses a method of harvesting lactoferrin and immunoglobulins from milk in which a conventionally obtained lactoserum is subjected to an adsorption treatment on a solid support, preferably silicon(IV) oxide, in a weakly basic milieu at a pH of more than 7.5, and the adsorbed proteins eluted with an acidic solution. Since they are only partly absorbed in this method, it is not especially appropriate for harvesting immunoglobulins alone.

The object of the present invention is to provide a simple and economical method of preparing a solution of lactic or colostric immunoglobulins or both.

This object is attained in accordance with the invention in that milk or colostrum or both are acidified to a pH of 4.0–5.5, subjected to cross-flow filtration in a filtration unit with a mean pore size of 0.1–1.2 $\mu$m, and the low-molecular components removed by means of further cross-flow filtration in another filtration unit with a limit of separation of 5,000–80,000 daltons.

The method in accordance with the invention takes ⅓ as much time as the conventional methods.

The invention will be further described with reference to the accompanying drawings, wherein.

Figure 1:
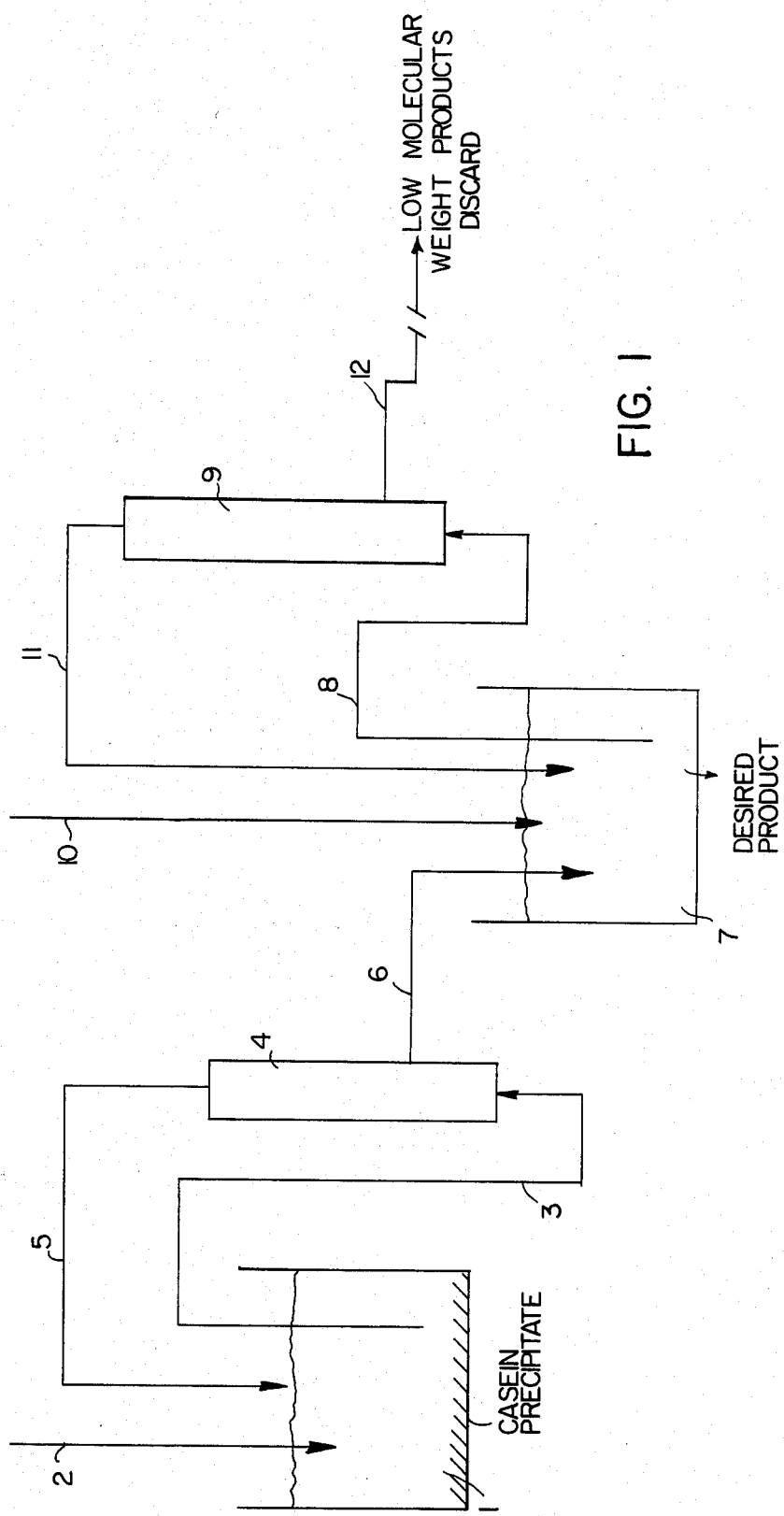
FIG. 1 is a flow chart of the method in accordance with the invention.

Referring now more particularly to the drawing, in FIG. 1 the milk and/or colostrum or both is acidified to a pH of 4.0–5.5 and preferably 4.8 in a container 1. Either dilute hydrochloric acid or an acetate buffer for example can be employed to acidify it. The milk and/or colostrum is preferably diluted before, after, or during acidification with a 0.3–1.5% electrolyte-solution, especially with a 0.9% solution, of sodium chloride, at a ratio of 1:2 for example, from a line 2. The acidified product is then pumped to a filtration unit 4 with a pore size of 0.1–1.2 $\mu$m through a line 3. This initial cross-flow dia-filtration, which is in the microfiltration range and preferably employs a hollow-fiber cartridge 4 with a pore size of 0.4 $\mu$m retains the precipitated casein. The filtrate is a clear solution that contains the immunoglobulins and low-molecular components. The hollow-fiber cartridges with a mean pore size of 0.1–1.2 $\mu$m that are employed for the initial cross-flow filtration are commercially available. They can be obtained in different lengths and have high membrane surfaces. Depending on the length of the cartridges employed, the microfiltration is carried out at an excess pressure of 0.1–1 bars. Temperature is not critical, and the process can be carried out at 4°–40° C. and preferably at room temperature. The casein retained in hollow-fiber cartridge 4 is returned to container 1 through a line 5. The volume of container 1 is kept constant by adding sodium-chloride solution. The resulting filtered solution is supplied to a container 7 through a line 6.

The solution is then conveyed from container 7 over a line 8 to another hollow-fiber cartridge 9 with a limit of separation of 5,000–80,000 daltons, in which the low-molecular components are removed from the immunoglobulin solution by means of further cross-flow filtration. The hollow-fiber cartridges employed for this further cross-flow filtration, which is in the ultrafiltration range, are also commercially available. A hollow-fiber cartridge with a limit of separation of 10,000 daltons is preferably employed. Sodium-chloride solution, preferably at a concentration of 0.9%, is conveyed to container 7 through a line 10. The purified immunoglobulin solution retained in hollow-fiber cartridge 9 is returned to container 7 through a line 11. The filtrate that contains the low-molecular components is removed from hollow-fiber cartridge 9 through a line 12. The second cross-flow filtration preferably comprises first, concentration, second, dia-filtration and, finally, concentration of the immunoglobulin solution to the desired protein content, 5–10% for example. The immunoglobulin solution is then filtration sterilized in a known way.

Milk and/or colostrum can be employed as the starting material for the method in accordance with the invention. When milk is employed, the gravid animals should be hyperimmunized in a known way to increase the yield of specific immunoglobulins.

When colostrum is employed as a starting material, the expensive hyperimmunization is unnecessary if the colostrum is obtained during the first few hours after birth. It has been discovered, surprisingly, that colostrum obtained shortly after birth contains a very high titer against various bacterial and viral antigens. This titer can be 50 to 100 times higher than that of milk obtained from immunized animals. A preferred starting material for the method in accordance with the invention is accordingly either a colostrum from non-hyperimmunized mammals or human colostrum, with colostrum obtained from cows up to 30 hours after calving and especially up to 5 hours after calving being particularly preferred.

Thus, in accordance with the invention for example, approximately 1 l of a filtration-sterilized 5% immunoglobulin solution appropriate for the treatment of bacterial and viral intestinal infections in both human and veterinary medicine can be obtained from 1 l of colostrum. The resulting immunoglobulin solution is especially appropriate for oral administration to premature infants and to any infant with intestinal infection and for intravenous administration in veterinary medicine.

The immunoglobulin solution obtained in accordance with the invention is clear and is stable without stabilizing additives at 37° C. Its lipid content is reduced to approximately 3% of that of the starting material. It exhibits only about 25% as much troublesome proteolytic activity as an immunoglobulin solution obtained from blood serum and stabilized with propiolactone and ultraviolet radiation. Its nonspecific complement binding equals that of known immunoglobulin preparations obtained from blood serum and modified with propiolactone or treated with enzymes.

The following antibody titers for example were established for a 5% immunoglobulin solution prepared in accordance with the invention:

| E. coli | 1:160 | (passive hemagglutination) |
|---|---|---|
| Ps. aeruginosa | 1:80 | " |
| Klebsiella | 1:160 | " |
| Staphylococci | 1:20 | " |
| Enterococci | 1:20 | " |
| Streptococci | 1:40 | " |
| Rotavirus | 1:32 | (complement-binding reaction). |

Figure 2:
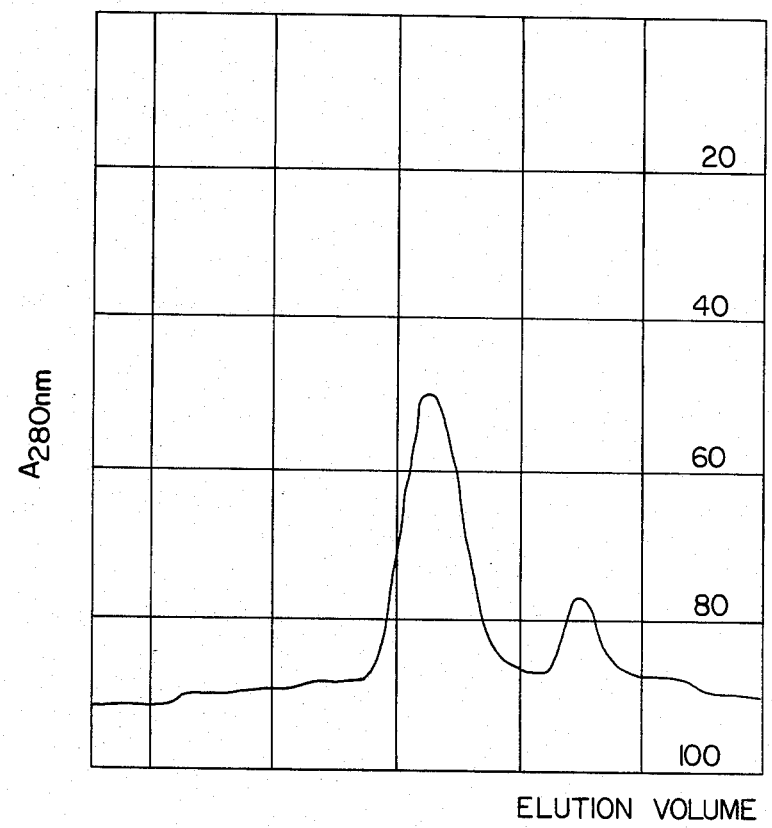
FIG. 2 is an elution curve of a gel chromatographed solution produced in accordance with the invention.

The gel chromatography on Dextrangel conventional for immunoglobulins revealed the elution curve illustrated in FIG. 2 for this immunoglobulin solution. The curve shows that the solution contains mainly IgG in addition to a slight proportion of lactalbumin. Immunoelectrophoresis demonstrated IgM, IgA, and secretory IgA. Electrophoresis on sheets of cellulose acetate revealed that the solution has a solids content of 77% gamma globulin (immunoglobulin), 1.2% lactalbumin, 3.4% beta globulins, and 17% alpha$_1$ and alpha$_2$ globulins.

This immunoglobulin was tested for antibacterial action on the mouse. The mice were infected i.p. with $1 \times 10^7$ of Ps. aeruginosa and then treated i.p. with 0.5 ml of the immunoglobulin solution. A control group was only infected. The results showed all the untreated animals dead 20 hours after infection, whereas 100% of those treated with the immunoglobulin solution were protected. This prophylactic action far exceeded that of a known immunoglobulin solution with the same protein concentration obtained form human serum or plasma.

The method in accordance with the invention will now be illustrated by means of examples.

EXAMPLE 1

Bovine colostrum obtained during the first 5 hours after calving was deep-frozen. 3.75 l of the deep-frozen colostrum was thawed. Its pH of 6.22 was adjusted to 4.8 by acidifying with 220 ml n HCl. The acidified colostrum was then maintained at 40° C. for 30 minutes and kept overnight at 4° C.

The acidified and precipitated colostrum was subsequently pumped into a container through a transfusion filter to remove the coarse particles and diluted to an overall volume of 6 l with a 0.9% solution of sodium chloride.

The resulting suspension was subjected to initial cross-flow filtration through two parallel hollow-fiber cartridges, each with a pore size of 0.4 µm and a surface of 0.5 m². The suspension was pumped through the two cartridges subject to dia-filtration for 4 hours along with 21 l of a 0.9% sodium-chloride solution at an excess pressure of 0.25 bars.

Even during the course of this initial cross-flow filtration, the filtrate was being subjected to a second cross-flow filtration through a hollow-fiber cartridge with a limit of separation of 10,000 daltons and a surface of 0.9 m² at an excess pressure of 1 bar. In the cartridge associated with the second filtration the solution was, first, concentrated, with the volume maintained constant at 5 l for 3 hours, second, dia-filtered with 20 l of a 0.9% sodium-chloride solution, and, finally, concentrated to a volume of 1.4 l with a protein content of 9.7%. The filtrate, containing the low-molecular components, was removed.

The resulting immunoglobulin solution was adjusted to a pH of 7.4 with 45 ml of 1N NaOH, filtration sterilized and bottled in quantities of 100 ml each.

EXAMPLE 2

13 l of bovine colostrum deep frozen as described in Example 1 were thawed. Its pH of 6.27 was adjusted to 4.8 by acidifying with 700 ml of 1N HCl. The resulting suspension was heated to 40° C. over 30 minutes and kept overnight at 4° C.

The suspension was then pumped into a container through a polyamide-gauze filter to remove the coarse particles and diluted with a 0.9% sodium-chloride solution to an overall volume of 26 l.

The initial cross-flow filtration of the suspension was then carried out through a hollow-fiber cartridge with a pore size of 0.4 µm, a surface of 3 m², and a fiber diameter of 1.2 mm, involving dia-filtration with 100 l of a 0.9% sodium-chloride solution at an excess pressure of 0.2–0.6 bars.

Even during the course of this initial cross-flow filtration, the filtrate was being subjected to a second cross-flow filtration through an apparatus consisting of three hollow-fiber cartridges, each with a limit of separation of 10,000 daltons and a surface of 1.4 m². In this apparatus the filtrate from the initial cross-flow filtration was, first, concentrated, second, dia-filtered with 100 l of a 0.9% sodium-chloride solution, and, finally, concentrated to an overall volume of 25 l with a protein content of 9.7%. The filtrate, containing the low-molecular components, was then removed.

The resulting immunoglobulin solution exhibited a protein content of 6% (as determined by means of a biuret reaction) and was filtration sterilized in a known way.

EXAMPLE 3

15 l of bovine colostrum deep frozen as described in Example 1 were thawed. Its pH of 6.20 was adjusted to 4.82 by acidifying with 1000 ml of 1n HCl. The resulting suspension was heated to 40° C. over 30 minutes and diluted to an overall volume of 30 l with a 0.9% sodium-chloride solution at 4° C.

The dilute suspension was subjected to initial cross-flow filtration through a hollow-fiber cartridge with a pore size of 0.4 µm and a surface of 2 m² at an excess pressure of 0.6 bars, involving dia-filtration with 150 l of a 0.9% sodium-chloride solution.

The filtrate from the initial cross-flow filtration, which was flowing at 25 l per hour, was supplied to an apparatus like that described in Example 2, consisting of three hollow-fiber cartridges, each with a limit of separation of 10,000 daltons and a surface of 1.4 m$^2$, for further cross-flow filtration. Concentration, with the volume being maintained constant at 25 l, was carried out first in this apparatus, followed by dia-filtration with 120 l of a 0.9% sodium-chloride solution and by concentrating the filtrate to a protein content of 7.8% at an excess pressure of 1.0–1.7 bars. The filtrate, containing the low-molecular components, was removed.

The resulting immunoglobulin solution was adjusted to a pH of 7.45 by adding approximately 130 ml of 1N NaOH, filtration sterilized with a multilayer filter, and bottled in portions.

The resulting immunoglobulin solution was composed of

| | |
|---|---|
| albumin | 1.5% |
| alpha globulins | 19% |
| beta globulins | 3.1% |
| immunoglobulin (gamma) | 77.4% |
| of which IgG | approx. 85% |
| IgM | 10%. |

It exhibited no demonstrable anticomplementary activity.

The following antibody titers were determined:

| Antibodies: | | | |
|---|---|---|---|
| | E. coli | 1:2560 | (passive hemagglutination) |
| | Ps. aeruginosa | 1:640 | " |
| | Klebsiella | 1:320 | " |
| | Staphylococci | 1:80 | " |
| | Enterococci | 1:40 | " |
| | Streptococci | 1:40 | " |

Viral

| Antibodies: | | | |
|---|---|---|---|
| | Varicella | <1:10 | (complement-binding reaction) |
| | Cytomegalo. | <1:10 | |
| | Rubella | <1:8 | |
| | Herpes | 1:20 | |
| | Rotavirus | 1:32. | |

It will be understood that the specification and examples are illustrative but not limitative of the present invention and that other embodiments within the spirit and scope of the invention will suggest themselves to those skilled in the art.

We claim:

1. In the preparation of a solution of lactic or colostric immunoglobulins by processing a lactic and/or colostric milk and precipitating the caseins, the improvement which comprises acidifying the milk to a pH of 4.0–5.5, subjecting the milk to cross-flow filtration in a filtration unit with a mean pore size of 0.1–1.2 μm, and subjecting the filtrate to a further cross-flow filtration in another filtration unit with a limit of separation of 5,000–80,000 daltons, thereby to separate the low-molecular components therefrom.

2. The method according to claim 1, wherein the colostrum is employed as the starting milk.

3. The method according to claim 1, wherein the starting material is colostrum from non-hyperimmunized mammals.

4. The method according to claim 1, wherein the starting milk is human colostrum.

5. The method according to claim 1, wherein the starting material is colostrum obtained from cows up to 30 hours after calving.

6. The method according to claim 1, wherein the starting milk is colostrum obtained from cows up to 5 hours after calving.

7. The method according to claim 1, wherein the milk prior to filtration is diluted with a 0.3–1.5% electrolyte solution.

8. The method according to claim 1, wherein the starting milk is acidified to a pH of 4.8.

9. The method according to claim 1, wherein the first filtration is effected with a hollow-fiber cartridge with a pore size of 0.4 μm.

10. The method according to claim 1, wherein the second filtration is effected with a hollow-fiber cartridge with a limit of separation of 10,000 daltons.

11. The method according to claim 1, wherein in the second filtration the solution is concentrated to a desired protein content and then filtration sterilized.

12. A solution for treating bacterial and viral infections produced by the process of claim 1.

* * * * *

UNITED STATES PATENT AND TRADEMARK OFFICE
CERTIFICATE OF CORRECTION

PATENT NO. : 4,644,056
DATED : February 17, 1987
INVENTOR(S) : Norbert Kothe, et al It is certified that error appears in the above-identified patent and that said Letters Patent is hereby corrected as shown below:

Column 5, line 26,   Insert -- Bacterial --

Signed and Sealed this

Twenty-fourth Day of November, 1987

Attest:

DONALD J. QUIGG

Attesting Officer   Commissioner of Patents and Trademarks